United States Patent [19]

Smith et al.

[11] Patent Number: 5,028,428

[45] Date of Patent: Jul. 2, 1991

[54] ANTI-IRRITANT AND DESENSITIZING COMPOSITIONS AND METHODS OF THEIR USE

[75] Inventors: Walter P. Smith, Stamford, Conn.; Nicholas J. Pelliccione, Brooklyn, N.Y.; Kenneth D. Marenus, Kings Park, N.Y.; Daniel H. Maes, Huntington, N.Y.

[73] Assignee: Estee Lauder Inc., New York, N.Y.

[21] Appl. No.: 230,444

[22] Filed: Aug. 9, 1988

[51] Int. Cl.$^5$ .................. A61K 35/78; A61K 7/42
[52] U.S. Cl. ............................ 424/195.1; 424/59; 424/60; 424/70; 424/73; 514/886; 514/887
[58] Field of Search ............... 424/195.1, 59, 60, 70, 424/73; 514/886, 887

[56] References Cited

U.S. PATENT DOCUMENTS

| | | |
|---|---|---|
| 4,569,839 | 2/1986 | Grollier et al. ............ 424/74 |
| 4,684,522 | 8/1987 | Marissal et al. ............ 424/195.1 |

FOREIGN PATENT DOCUMENTS

| | | |
|---|---|---|
| 328598 | 11/1920 | Fed. Rep. of Germany . |
| 961022 | 3/1957 | Fed. Rep. of Germany . |
| 2128228 | 3/1971 | France . |
| 2609395 | 2/1988 | France . |
| 62-298523 | 12/1987 | Japan . |
| 2092445 | 8/1982 | United Kingdom . |

OTHER PUBLICATIONS

Lewis et al., *Medical Botany*, p. 387, (1977).
Steinmetz, *Codex Vegetabilis*, reference no. 330, (1957).
Lust, *The Herb Book*, p. 242, (1974).
Chemical Abstracts, 82:2734j, (1975).
Chemical Abstracts, 97:188327s, (1982).

*Primary Examiner*—John W. Rollins
*Attorney, Agent, or Firm*—Richard M. Barnes; Doreen F. Shulman; Michael P. Morris

[57] ABSTRACT

Compositions and methods for reducing the adverse reaction of skin to chemicals and compositions that contact the skin, e.g., topical cosmetic and pharmaceutical preparations, and to contact physical irritants. The active ingredient of the composition of the invention comprises a hydro-alcoholic extract of Cola nitida.

11 Claims, No Drawings

ANTI-IRRITANT AND DESENSITIZING COMPOSITIONS AND METHODS OF THEIR USE

BACKGROUND OF THE INVENTION

This invention relates to compositions for reducing adverse reactions of the skin to chemicals and compositions that contact the skin, e.g., topical cosmetic and pharmaceutical compositions, and for reducing such adverse reactions caused by certain kinds of physical contact.

Exposure of human skin to chemicals contained in topical cosmetic and pharmaceutical compositions can result in adverse reactions to the skin, including irritation response and contact sensitization of the skin. As used herein, the term cosmetic and pharmaceutical compositions is used in the widest sense of the term, and encompasses any composition that is applied to the skin for a beneficial effect. As used herein, contact sensitization of the skin refers to adverse systemic immunological reactions of the skin, e.g., itching, burning, swelling or redness. Irritation response of the skin involves similar symptoms in which the systemic immune system plays no role.

A small, but significant segment of the population is particularly prone to such irritation response and contact sensitization. As a consequence, the use of a wide variety of topical preparations for the skin by this segment of the population is, at best, an unpleasant task. For example, compositions containing paramino benzoic acid (e.g., sunscreens) or Balsam of Peru are known to cause contact sensitization, and certain chemicals, e.g., vasodilators and surfactants are known to cause irritation response when used by certain persons.

In addition, certain types of physical contact with human skin can cause irritation response of the skin. For example, the removal of hair from human skin by waxing methods is known to cause irritation to most, if not all, persons who have waxing treatments. Hereinafter, the types of physical contact that cause irritation response of human skin are referred to as "contact physical irritants."

SUMMARY OF THE INVENTION

An object of this invention is to provide a composition and method for reducing the irritation response and contact sensitization of human skin to chemicals and compositions that contact the skin, e.g., topical cosmetic and pharmaceutical preparations.

Another object of this invention is to provide a composition and method for reducing the irritation response of human skin to contact physical irritants.

We have discovered that compositions containing a hydroalcoholic extract of Cola nitida in a carrier are useful for reducing adverse reactions of the skin to chemical irritants and to contact physical irritants. Preferably, the composition of the invention comprises at least 2.5% by weight of the hydroalcoholic extract of Cola nitida.

As used herein, the term "carrier" shall include materials that are suitable for use in contact with the skin and which, when combined with the Cola nitida extract in the composition of the invention, take a form that is suitable for application to the skin, e.g., the form of a liquid, gel, ointment, cream, lotion or the like.

The compositions of the invention may be applied in effective amounts to the skin in any suitable manner at about the time the skin is exposed to a chemical irritant or a contact physical irritant. Preferably, they are applied to the skin in an effective amount shortly before (e.g., less than about half an hour before, preferably less than about 15 minutes before) the skin is exposed to a chemical or contact physical irritant. It is within the scope of the invention, however, to apply the composition of the invention simultaneously with (e.g., as part of a composition containing a chemical irritant) or shortly after (e.g., less than about half an hour after, preferably less than about 15 minutes after) the skin is exposed to a chemical or contact physical irritant.

In use, the composition of the invention prevents the induction of any noticeable adverse systemic immunological reaction of the skin (i.e., it prevents the induction of contact sensitization) in some cases and reduces the extent of contact sensitization in other cases. Similarly, in use the composition of the invention prevents the onset of an irritation response to the skin in some cases and reduces the extent of irritation response to the skin in other cases.

DETAILED DESCRIPTION OF THE INVENTION

Cola nitida (also known as Cola nitida semen) is a plant that includes Cola nuts. Extracts useful in the composition of the invention may be obtained by crushing the Cola nuts and then extracting the crushed nuts with a hydroalcoholic solution (e.g., a 50% aqueous solution of ethyl alcohol at 25° C.). After filtering, the extract is preferably concentrated by drying (e.g., spray drying) to obtain either a solid or liquid extract (depending on the extent of drying). Suitable Cola nitida extracts may be obtained from Indena S.P.A., Gruppo Inverni Della Beffa, Milan, Italy.

Suitable hydroalcoholic extracts of Cola nitida for use in this invention include hydroalcoholic extracts of Cola nitida that have been treated (either before or after they are concentrated by drying) to alter the color of the extract (e.g., to lighten its color) and/or to diminish its odor. Such treatment can be accomplished, for example, by chromatographic techniques.

In one embodiment of this invention, the composition of the invention comprises at least 2.5% by weight of Cola nitida extract in a suitable carrier. In other embodiments, the composition comprises at least 5% by weight of the Cola nitida extract (e.g., 10-15% by weight of the extract).

Upon application to the skin, the composition of the invention is effective in reducing adverse reactions of the skin to a number of chemical irritants. For example, when a composition containing 10% by weight of Cola nitida extract was applied by a panel of persons (who were chosen to be on the panel because of their sensitivity to a variety of irritant compounds) just before the persons applied to their skin a known irritant (Balsam of Peru), the irritation response of the panel to the irritant was significantly reduced. In addition, panelists who were known to exhibit an irritation response to paramino benzoic acid containing sunscreens applied a composition containing 10% by weight of Cola nitida extract composition prior to applying such a sunscreen with the following results: 86% of the panelists demonstrated a noticeable improvement in resistance to sunscreen irritation (slightly more than half of which demonstrated a highly significant improvement), 10% of the panelists had no change in response to sunscreen irritation and 3% (one person) had a decrease in resistance to sunscreen irritation.

Preferably, the compositions of the invention are applied to the skin shortly before (about 30 minutes or less, preferably about 15 minutes or less) a cosmetic or pharmaceutical composition containing a chemical irritant is applied to the skin.

The composition of the invention may also be applied shortly after (less than about 30 minutes after, preferably less than about 15 minutes after) a cosmetic or pharmaceutical composition containing a chemical irritant is applied to the skin. In addition, the Cola nitida extract may be included in effective amounts in compositions containing chemical irritants, thereby permitting the simultaneous application of the Cola nitida extract and the irritant to the skin.

The composition of the invention may also be applied to the skin shortly before (about 30 minutes or less, preferably about 15 minutes or less) the skin is waxed for the purpose of removing hair therefrom. We have found that the use of our composition in such a manner reduces the irritation resulting from removing hair by such waxing techniques. The composition of the invention may also be applied shortly after (less than about 30 minutes after, preferably less than about 15 minutes after) the skin is waxed for the purpose of removing hair therefrom. We believe also that the composition of the invention would be useful to reduce the irritation response of the skin to other contact physical irritants such as, for example, harsh environmental conditions and abrasive clothing.

A wide variety of materials may be used as carriers in the composition of the invention. Examples of such carriers include hydroalcoholic solutions and water and oil emulsions. In addition, the compositions of the invention may include other active ingredients for the skin as well as one or more fragrances, preservatives, emulsifiers, and other materials of the type that are conventionally included in cosmetic and pharmaceutical compositions. Among the wide range of active ingredients that may be included in the composition of the invention, but which do not comprise part of the invention, are vitamins, sunscreens, antioxidants, free radical scavengers, lipids, glycolipids, and other materials that have desirable cosmetic or pharmaceutical effects on the skin.

The following non-limiting Example illustrates a composition of the present invention.

EXAMPLE

A formulation comprising an oil in water emulsion was prepared by combining the following ingredients in the sequence and manner described below:

EXAMPLE 1

| Ingredient | Parts By Weight |
| --- | --- |
| Sequence 1 | |
| Hetester PCA (an oil) | 10.00 |
| Hetester PHA (an oil) | 5.00 |
| Parabens (a preservative) | 0.15 |
| Glyceryl mono stearate (a wax) | 1.30 |
| MYRJ 52 (an emulsifier) | 1.20 |
| Emerest 2486 (an oil) | 1.00 |
| Sequence 2 | |
| Cola nitida Powder | 10.00 |
| Deionized Water | 38.15 |
| Butylene Glycol (a solubilizer) | 6.00 |
| Emeressence 1160 (a preservative) | .05 |
| Parabens (a preservative) | .35 |
| Sequestrene (a chelating agent) | .10 |
| Sequence 3 | |
| Carbopol 934 (2% aqueous solution) (a thickener) | 20.00 |
| Sequence 4 | |
| Deionized Water | 3.00 |
| TEA 99% (a neutralizer) | 0.40 |
| Sequence 5 | |
| Deionized Water | 3.00 |
| Germall 115 (a preservative) | 0.3 |

The above ingredients were combined by the following procedure:

(1) the Sequence 1 ingredients were combined and heated to 78° C., with mixing;

(2) the Sequence 2 ingredients were combined and heated to 78° C., with mixing, until the Parabens dissolve;

(3) the Sequence 3 ingredient was added to the Sequence 2 ingredients, with mixing;

(4) the Sequence 1 ingredients were added to the Sequence 3 ingredients, with mixing;

(5) the mixture of the Sequence 1-3 ingredients was cooled to 45° C.;

(6) the Sequence 4 ingredients were added to the cooled mixture of Sequence 1-3 ingredients, with mixing;

(7) the resulting mixture of Sequence 1-4 ingredients was cooled to 38° C.;

(8) the Sequence 5 ingredients were added to the cooled mixture of Sequence 1-4 ingredients, with mixing; and (9) the mixture of Sequence 1-5 ingredients was cooled to 25° C.

We claim:

1. A method of reducing the adverse reaction of skin to chemicals contained in topical cosmetic and pharmaceutical preparations and to contact physical irritants, said method comprising applying to the skin an effective amount of a composition comprising at least about 2.5% by weight of a hydroalcoholic extract of Cola nitida in a carrier suitable for use in contact with the skin, the composition being applied to the skin shortly before, simultaneously with, or shortly after the skin is exposed to a chemical irritant in a cosmetic or pharmaceutical composition or to a contact physical irritant.

2. The method of claim 1 wherein the composition is applied to the skin shortly before the skin is exposed to a chemical irritant or to a contact physical irritant.

3. The method of claim 2 wherein the composition is applied to the skin shortly before a composition containing paramino benzoic acid or Balsam of Peru is applied to the skin.

4. The method of claim 3 wherein the composition is applied to the skin about 15 minutes or less before a composition containing paramino benzoic acid or Balsam of Peru is applied to the skin.

5. The method of claim 2 wherein the composition is applied to the skin shortly before that skin is waxed for the purpose of removing hair therefrom.

6. The method of claim 5 wherein the composition is applied to the skin about 15 minutes or less before that skin is waxed for the purpose of removing hair therefrom.

7. The method of claim 2 wherein the composition is applied to the skin about 15 minutes or less before the skin is exposed to a chemical irritant or to a contact physical irritant.

8. The method of claim 2 wherein the extract o nitida comprises at least about 5% by weight of the total composition.

9. The method of claim 2 wherein the extract of Cola nitida comprises about 10–15% by weight of the total composition.

10. The method of claim 1 wherein the extract of Cola nitida comprises at least about 5% by weight of the total composition.

11. The method of claim 1 wherein the extract of Cola nitida comprises about 10–15% by weight of the total composition.

* * * * *

UNITED STATES PATENT AND TRADEMARK OFFICE
CERTIFICATE OF CORRECTION

PATENT NO. : 5,028,428
DATED : July 2, 1991
INVENTOR(S) : Smith et al.

It is certified that error appears in the above-indentified patent and that said Letters Patent is hereby corrected as shown below:

Col. 3, line 55, delete "Example 1".

Col. 6, line 3, After "extract" delete "o" and insert therefor
—of Cola—.

Signed and Sealed this

Twenty-seventh Day of September, 1994

Attest:

BRUCE LEHMAN

*Attesting Officer*         *Commissioner of Patents and Trademarks*